United States Patent [19]

Miyazaki et al.

[11] Patent Number: 5,313,936
[45] Date of Patent: May 24, 1994

[54] INDUSTRIAL ENDOSCOPE APPARATUS

[75] Inventors: Atsushi Miyazaki, Hachioji; Seiji Kimura, Hino, both of Japan

[73] Assignee: Olympus Optical Co., Ltd., Tokyo, Japan

[21] Appl. No.: 10,994

[22] Filed: Jan. 29, 1993

[30] Foreign Application Priority Data

Apr. 20, 1992 [JP] Japan .................................. 4-99560

[51] Int. Cl.$^5$ .............................................. A61B 1/04
[52] U.S. Cl. ........................................................ 128/6
[58] Field of Search ........................ 128/6; 248/917; 312/7.2, 223.2, 223.3

[56] References Cited

U.S. PATENT DOCUMENTS

| | | | |
|---|---|---|---|
| 4,475,539 | 10/1984 | Konomura | 128/6 |
| 4,736,734 | 4/1988 | Matsuura et al. | 128/6 |
| 4,846,155 | 7/1989 | Kimura | 128/6 |
| 4,941,456 | 7/1990 | Wood et al. | 128/6 |
| 4,964,018 | 10/1990 | Mallory et al. | 248/917 X |
| 5,161,028 | 11/1992 | Kawata et al. | 248/917 X |

FOREIGN PATENT DOCUMENTS 59-70384  4/1984  Japan .
3-27203   3/1991  Japan .

Primary Examiner—Richard J. Apley
Assistant Examiner—Beverly A. Meindl
Attorney, Agent, or Firm—Armstrong, Westerman, Hattori, McLeland & Naughton

[57] ABSTRACT

An industrial endoscope apparatus including an endoscope which is to be inserted into an inspection portion, a control device for controlling the endoscope, a light source device for supplying an illumination light to a distal end portion of the endoscope, a CRT monitor for displaying an image of an object, a casing in which the control device, the light source device and the CRT monitor are contained within one unit, and a fixing member for detachably fixing the CRT monitor to the casing.

9 Claims, 4 Drawing Sheets

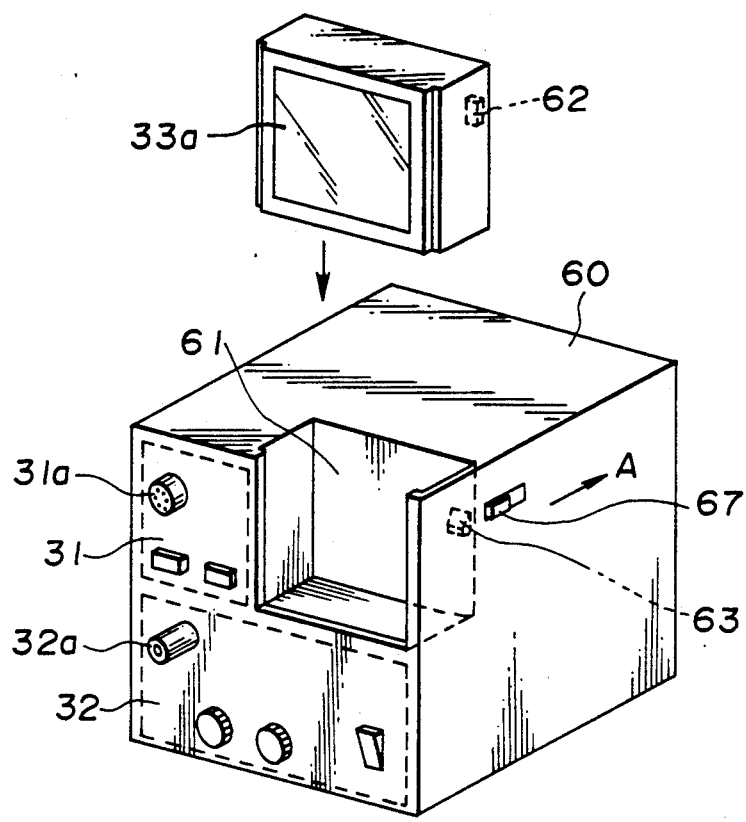
FIG. 6
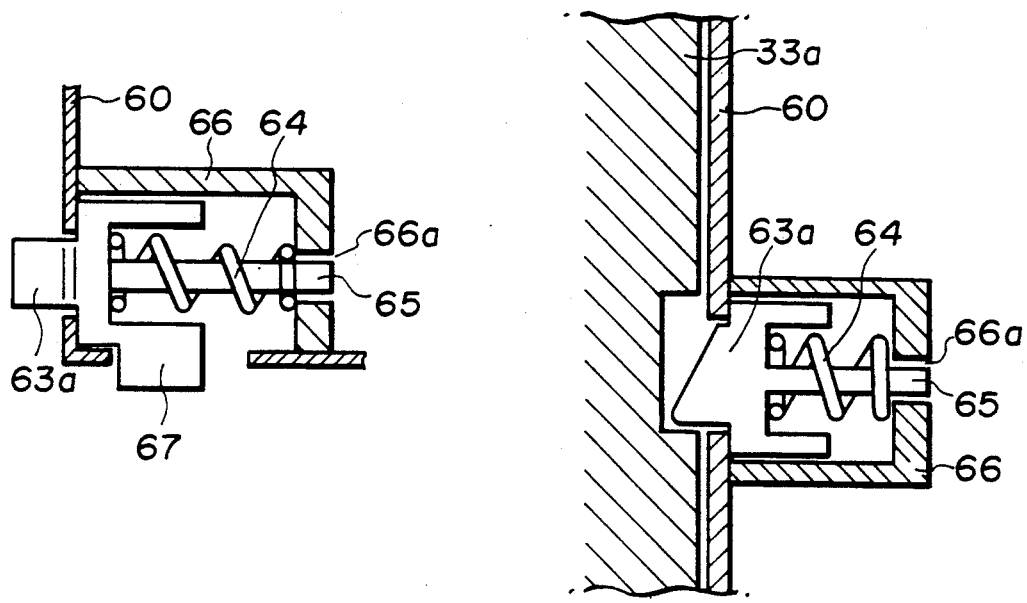
FIG. 7
FIG. 8

INDUSTRIAL ENDOSCOPE APPARATUS

BACKGROUND OF THE INVENTION

1. Field of the Invention

The present invention relates to an industrial endoscope apparatus of the type in which a monitor can be detachably mounted on a casing in which a control device and a light source device are formed as one device.

2. Description of the Related Art

Endoscopes are classified into medical endoscopes used for observing organs in a body cavity and industrial endoscopes used for observing the interior of a boiler, a turbine, an engine or a chemical plant.

In an industrial endoscope apparatus used for inspecting an object to be inspected, such as a boiler, a turbine or an engine, an industrial endoscope and a peripheral device are generally carried to the site where the object to be inspected is placed for inspection.

In the case of an industrial endoscope apparatus which employs a fiber scope as the industrial endoscope, only a light source device is required to be carried as a peripheral device to the site where the object to be inspected is placed for inspection in addition to the fiber scope. Thus, it is easy to carry such an endoscope apparatus from one place to another.

In the case of an industrial endoscope apparatus employing an electronic endoscope as the industrial endoscope, however, a control device, a light source device and a monitor must be carried to the inspection site as the peripheral devices in addition to the electronic endoscope.

Hence, Japanese Patent Laid-Open No. Sho 59-70384 discloses the industrial endoscope apparatus in which the light source device and the monitor are formed as one device in order to improve the portability thereof. Japanese U. M. Laid Open Hei 3-27203 discloses the industrial endoscope apparatus in which the monitor can be mounted later on a peripheral device in order to give the workability priority. U.S. Pat. No. 4,941,456 discloses the industrial endoscope apparatus in which a control device, a light source device, a video processor and a power source device are formed as one device while a monitor is provided independently of these devices.

However, in an industrial endoscope apparatus in which the individual components are provided separately or in which the peripheral device and the monitor are formed separately, the plurality of devices, including the monitor and the peripheral device, must be transported for inspection in addition to the endoscope. Thus, the transportation of the endoscope apparatus is not easy.

The industrial endoscope apparatus in which the peripheral device and the monitor are formed as one device in order to improve the portability of the apparatus suffers from a problem in that it is difficult to look at the monitor depending on the posture or position of the operator because the monitor is provided at a fixed position.

The industrial endoscope apparatus in which the monitor is connected to the peripheral device after the transportation of the apparatus has a drawback in that it is difficult to carry the apparatus from one place to another and in that the workability thereof is deteriorated because the apparatus requires a system setting each time inspection is conducted.

SUMMARY OF THE INVENTION

An object of the present invention is to provide an industrial endoscope apparatus in which a monitor and a peripheral device can be united as one unit during transportation in order to improve the portability of the apparatus.

Another object of the present invention is to provide an industrial endoscope apparatus in which a monitor can be disposed separately from a peripheral device during inspection in order to improve the workability of the inspection operation.

To achieve the above-described objects, the present invention provides an industrial endoscope apparatus which comprises an endoscope which is to be inserted into an inspection portion, a control device for controlling the endoscope, a light source device for supplying an illumination light to a distal end portion of the endoscope, a CRT monitor for displaying an image of an object, a casing in which the control device, the light source device and the CRT monitor are accommodated as one unit, and a fixing means for detachably fixing the CRT monitor to the casing.

Other objects and advantages of the invention will become apparent from the following description taken in connection with the accompanying drawings.

BRIEF DESCRIPTION OF THE DRAWINGS

FIG. 6 is a perspective view showing the relation between a LCD monitor and a casing according to a third modification;

FIG. 7 is a horizontal cross-sectional view showing a connecting portion for connecting the LCD monitor and the casing shown in FIG. 6; and FIG. 8 is a vertical cross-sectional view of the connecting portion of FIG. 7.

DETAILED DESCRIPTION OF THE PREFERRED EMBODIMENTS

Figure 1:
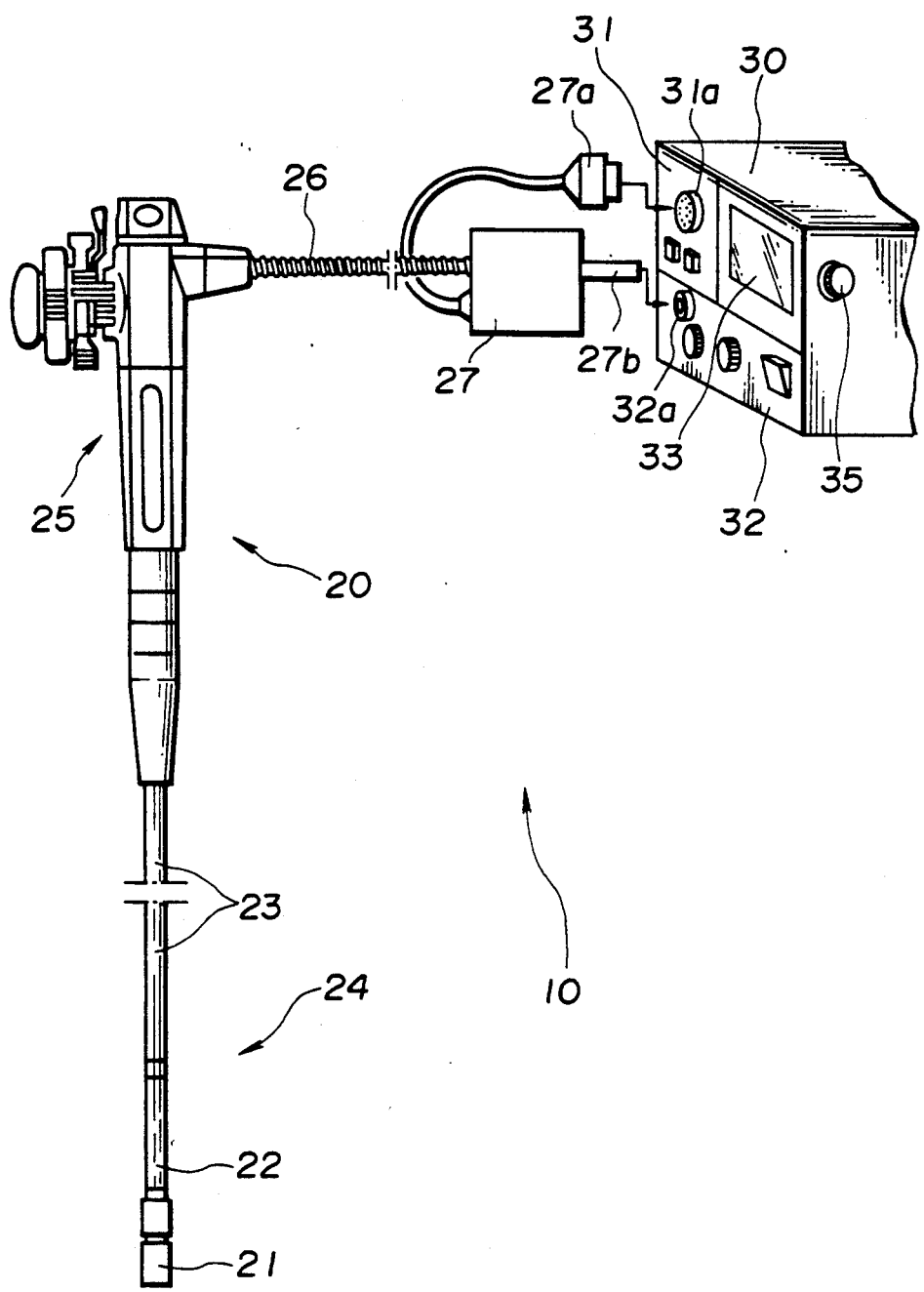
FIG. 1 is a schematic view of an industrial endoscope apparatus, showing an embodiment of the present invention.

An industrial endoscope apparatus 10 shown in FIG. 1 includes an electronic endoscope 20 which can be inserted into a boiler, a turbine, an engine or a chemical plant, a control device 31 for controlling the electronic endoscope 20, a light source device 32 for supplying an illumination light, a monitor 33 for displaying an observed image, a casing 30 in which the control device 31, the light source device 32 and the monitor 33 are accommodated as one device, and so on.

The electronic endoscope 20 includes an inserted portion having a distal end portion 21, a curved portion 22 that can be curved, and a flexible portion 23 which are joined to each other in that order, and an operated portion 25 provided at the rear end of the inserted portion 24. A universal code 26 extends from the side of the operated portion 25. The universal code 26 has a connector portion 27 at the end portion thereof.

The control device 31 provided in the casing 30 has a control unit for controlling the curving angle of the curved portion 22 of the electronic endoscope 20, and a camera control unit. The electronic endoscope 20 is electrically connected to the control device 31 by connecting a control connector 27a provided at the distal end of an electric cable extending from the connector portion 27 of the universal code 26 to a connector receptor 31a of the control device 31.

The light source device 32 provided in the casing 30 has a light source for illuminating a portion to be observed by the electronic endoscope 20. The illumination light can be supplied to the distal end portion of the endoscope by connecting a light source connector 27b provided at the connector portion 27 of the universal code 26 to a connector receptor 32a of the light source device 32.

The monitor 33 mounted on the casing 30 is of the CRT type, and can be mounted on or removed from the casing 30 by tightening or loosening a monitor mounting/removing knob 35.

Figure 2:
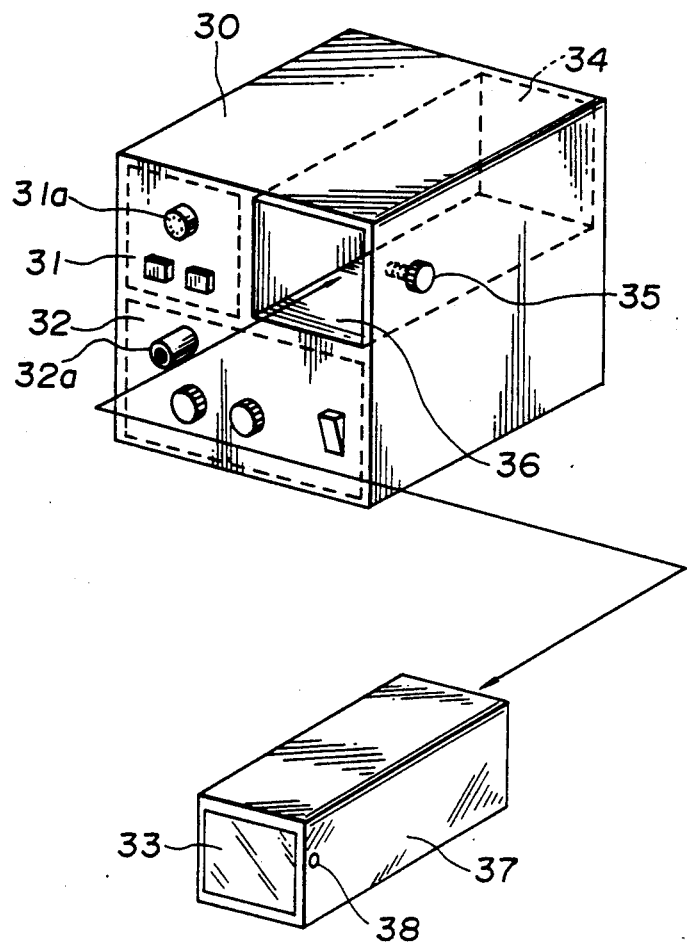
FIG. 2 is a perspective view showing the relation between a monitor and a casing according to the embodiment of the present invention.

That is, whereas the control device 31 and the light source device 32 are provided in the casing 30, as shown in FIG. 2, a monitor mounting space portion 34 into which the CRT monitor 33 is to be mounted integrally with the other devices is provided in the casing 30. An opened portion 36 is formed on the front side of the casing 30 as an opening from which the monitor 33 is mounted in the monitor mounting space portion 34, and the monitor mounting/removing knob 35 having an externally threaded portion is provided on the side surface of the casing. A positioning hole 38 having an internally threaded portion to be engaged with the monitor mounting/removing knob 35 is provided on a side surface 37 of the CRT monitor 33.

The operation of the industrial endoscope apparatus 10 arranged in the manner described above will now be described.

First, the industrial endoscope apparatus 10 with the monitor 33 accommodated in the monitor mounting space portion 34 of the casing 30 in which the control device 31 and the light source device 32 are provided and with the monitor mounting/removing knob 35 tightened is transported to the site where the object to be inspected is placed. After the industrial endoscope apparatus 10 has been carried to the inspection site, the monitor 33 accommodated in the casing 30 is removed. The monitor 33 is removed from the casing 30 by loosening the monitor mounting/removing knob 35 provided on the side surface of the casing 30 and thereby removing the monitor mounting/removing knob 35 from the positioning hole 38 provided in the side surface 37 of the monitor 33.

Next, the control connector 27a of the connector portion 27 provided at the distal end portion of the universal code 26 of the electronic endoscope 20 is connected to the connector receptor 31a of the control device 31. The light source connector 27b of the connector portion 27 is connected to the connector receptor 32a of the light source device 32. Thereafter, the endoscope inspection is conducted.

The monitor 33 which has been removed from the casing 30 is disposed at a position and in a direction in which the inspector can easily look at the screen thereof.

In the present invention, since the industrial endoscope apparatus 10 with the monitor 33 accommodated into the monitor mounting space portion 34 formed in the casing 30 and screwed to the casing 30 in which the control device 31 and the light source device 32 are provided is carried to the inspection side where the inspection of the object to be inspected takes place, the portability of the apparatus 10 is greatly improved.

Furthermore, the industrial endoscope 10 has been transported to the inspection side, the monitor 33 can be readily removed from the monitor mounting space portion 34 only by loosening the monitor mounting/removing knob 35 fixed to the casing 30.

Furthermore, after the removal of the monitor 33 from the casing 30, the casing 30 can be located at a position which is convenient to the inspector while the monitor 33 can be located at a position and in a direction where the inspector can easily look at it. Accordingly, the inspector can perform the inspection operation in a comfortable posture.

If an urging means for pushing out the monitor 33 is provided at the deep portion of the monitor mounting space portion 34 provided in the casing 30, it is possible to protrude the monitor 33 by a predetermined distance from the front surface of the casing 30 when the monitor mounting/removing knob 35 is loosened. As a result, the monitor 33 can be more easily removed from the casing 30.

Figure 3:
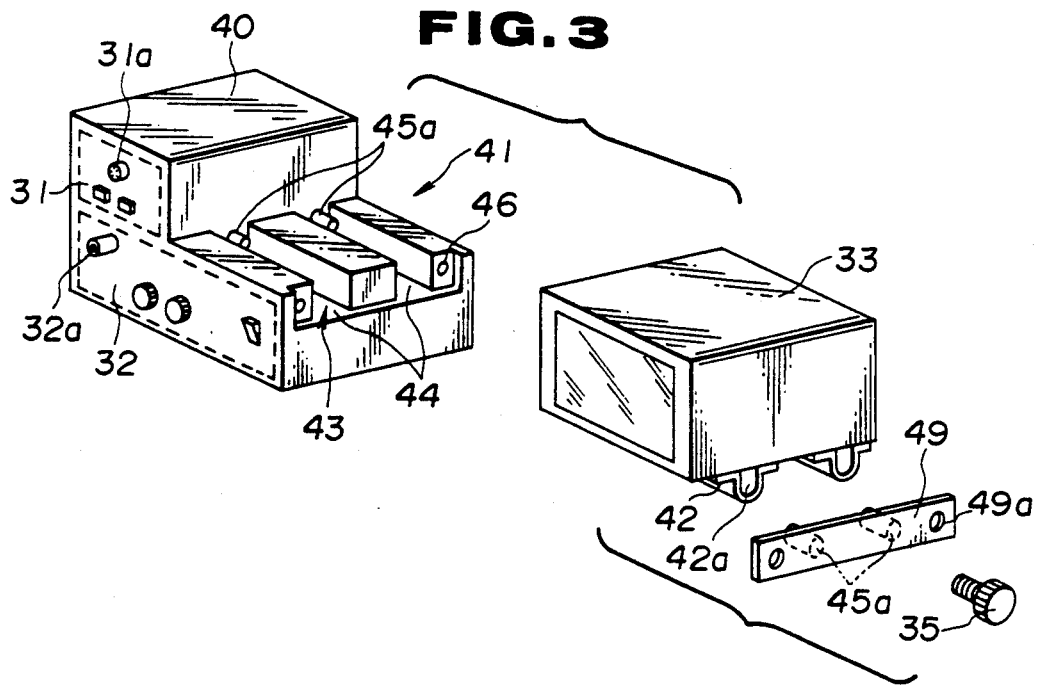
FIG. 3 is a perspective view showing the relation between a monitor and a casing according to a first modification.

The monitor 33 may also be accommodated in the casing 30 by forming a monitor mounting portion in the casing 30 in place of the monitor mounting space portion 34. FIG. 3 shows a first modification of the casing.

As shown in FIG. 3, in the first modification, a notch/shoulder portion 41 is formed in a casing 40 as the monitor mounting portion, and the monitor 33 is mounted in this notch/shoulder portion 41.

That is, a plurality of coupling members 42 each having a through-hole 42a are disposed at the bottom of the monitor 33 which can be mounted on and removed from the casing 40.

In the casing 40 into which the monitor 33 is mounted, the notch/shoulder portion 41 is formed on a box member in which the control device 31 and the light source device 32 are disposed. In the notch/shoulder portion 41, a plurality of groove portions 44 corresponding to the plurality of coupling members 42 disposed on the monitor 33 are provided in a direction perpendicular to the control device 31.

Positioning pins 45a are disposed on the portion of the wall surface of the notch/shoulder portion 41 which is located on the side of the control device and within the groove portions. The positioning pins 45a can be inserted into the through-holes 42a of the coupling members 42 provided on the monitor 33 and thereby locate the monitor 33 at position and prevent the monitor 33 coming off in the direction perpendicular to the control device 31.

In the notch/shoulder portion 41, shoulder portions 43 and internally threaded portions 46 are also formed to dispose and fix a fixing member which will be described later.

The monitor 33 is mounted in or removed from the casing 40 arranged in the manner described above in the manner described below.

When the monitor 33 is to be mounted in the casing 40, the coupling members 42 provided on the monitor 33 are aligned with the groove portions 44 provided in the casing 40. The coupling members 42 of the monitor 33 are moved toward the control device to insert the positioning pins 45a into the through-holes 42a of the coupling members 42 to a predetermined position and thereby position the monitor 33.

Next, the monitor 33 is fixed at a position where it is pressed to the wall surface of the casing 40 located on the side of the control device.

More specifically, after the monitor 33 is temporarily placed in the notch/shoulder portion 41 in the manner described above, a fixing member 49 is disposed at the portions of the shoulder portions 42 of the casing 40 which are located remote from the control device. At that time, positioning pins 45b provided on the fixing member 49 are inserted into the through-holes 42a of the coupling members 42 provided on the monitor 33. The monitor mounting/removing knobs 35 are inserted into through-holes 49a formed in the fixing member 49 and then brought into engagement with the internally threaded portions 46 formed in the casing 40 to fix the monitor 33 to the casing 40.

When the monitor 44 is to be removed from the casing 40, it can be readily removed from the notch/shoulder portion 41 of the casing 40 by loosening the monitor mounting/removing knobs 35 and thereby removing the fixing member 49. The other structure and operation are the same as those of the first embodiment.

Figure 4:
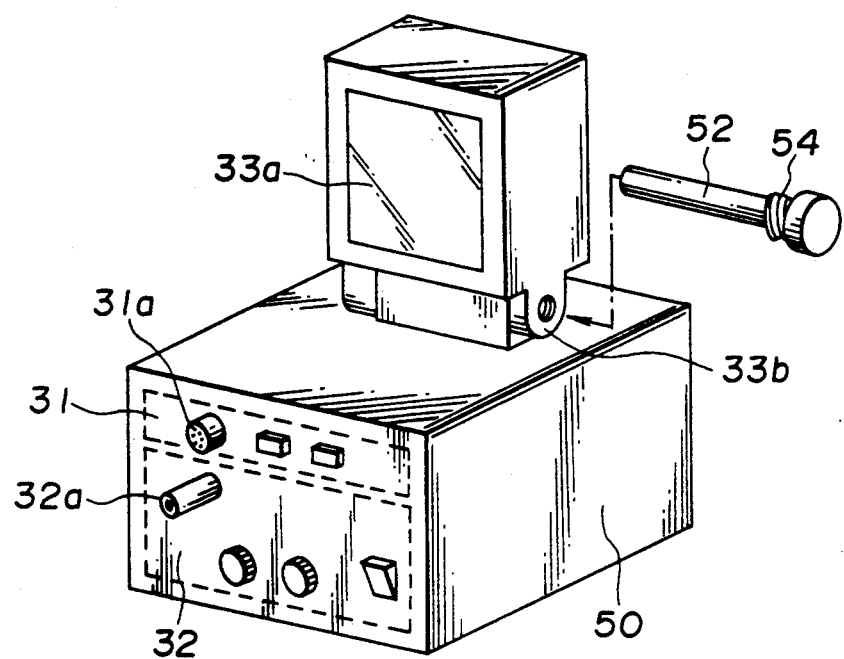
FIG. 4 is a perspective view showing the relation between a LCD monitor and a casing according to a second modification.
Figure 5:
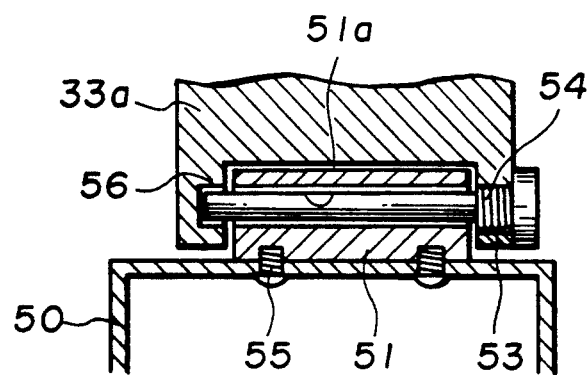
FIG. 5 is a cross-sectional view showing the connection between the LCD monitor and the casing shown in FIG. 4.

The industrial endoscope apparatus 10 may also be arranged by employing an LCD type monitor in place of the CRT monitor 33. FIGS. 4 and 5 show a second modification.

In this embodiment, an LCD monitor 33a which can be mounted on and removed from the casing is used in place of the CRT monitor 33, as shown in FIG. 4. The monitor 33a is coupled to a casing 50 by screwing a connection pin 52 into a monitor mounting member 51 fixed to the casing 40.

As shown in FIG. 5, the monitor mounting member 41 having a through-hole 51a is fixed to the ceiling surface of the casing 50 by means of a plurality of fixing screws 55.

A pair of convex portions 33b are formed on the bottom of the monitor 33a as if they hold the monitor mounting member 51. A blind hole 56 into which the connection pin 52 is to be inserted is formed in one of the convex portions 33b. An internally threaded portion 53 to be engaged with an externally threaded portion of the connection pin 52, which will be described later, is formed in the other of the convex portions 33b.

An externally threaded portion 54 to be engaged with the internally threaded portion 53 is formed at the proximal end portion of the connection pin 52 for connecting the monitor 33a to the casing 50.

The distal end side of the externally threaded portion 54 is a round bar having a diameter smaller than the diameter of the internally threaded portion 54 formed in the convex portion 33b.

The monitor 33a is mounted in and removed from the casing 50 arranged in the manner described above in the manner described below.

When the monitor 33a is to be mounted in the casing 50, the pair of convex portions 33b formed on the monitor 33a are disposed as if they hold the monitor mounting member 51. Next, The connection pin 52 is inserted into the internally threaded portion 53 of the monitor 33, the through-hole 51a of the monitor mounting member 51 and then the blind hole 56, and the externally threaded portion 54 formed on the proximal end portion of the connection pin 52 is then brought into engagement with the internally threaded portion 53, whereby the monitor 33a is fixed to the casing 50.

When the monitor 33a is removed from the casing 50, it can readily be removed from the monitor mounting portion 51 of the casing 50 by removing the connection pin 52.

Thus, the use of the small and light LCD monitor 33a enables the provision of a small and light industrial endoscope apparatus which can be more easily carried from one place to another when compared with the case in which the CRT monitor 33 is used.

Furthermore, since the monitor 33a mounted on the ceiling surface of the casing 50 can be fixed at a desired angle, it can be quickly set at an angle which ensures that the inspector can view it comfortably without being removed from the casing 50.

In order to carry the industrial endoscope apparatus 10 to the inspection site safely, the connection pin 52 may be fixed with the display surface of the monitor 33a being in contact with the ceiling surface of the casing 50. The other structure and operation are the same as those of the previous embodiment.

FIGS. 6 through 8 show a modification of the industrial endoscope apparatus 10 which employs the LCD monitor 33a.

In this embodiment, the monitor 33a is detachably housed in a recessed portion 61 formed in a casing 60, as shown in FIG. 6. The monitor 33a is fixed to the casing 60 by bringing a fixing hook 63 provided on the casing 60 into engagement with a shoulder portion 62 provided in the rear surface of the monitor 33a.

As shown in FIGS. 7 and 8, the fixing hook 63 for fixing the monitor 33a includes a claw 63a which is inserted into the shoulder portion 62 formed in the rear surface of the monitor 33a, a spring 64 which is the urging means of the fixing hook 63, a shaft 65 which is inserted into the inner diameter portion of the spring 64, and a moving claw 67 for moving the fixing hook 63 against the urging force. The shaft 65 formed in the fixing hook 63 is inserted into a guide hole 66a of a guide block 66 provided in the rear surface of the recessed portion 61 of the casing 60, and the claw 63 is pressed against the monitor by the urging force of the spring 64.

The monitor 33a is mounted on and removed from the casing 60 arranged in the manner described above in the manner described below.

When the monitor 33a is to be mounted on the casing 60, the monitor 33a is first positioned in the recessed portion 61 and then pushed downward. At that time, the monitor 33a makes contact with the claw 63a of the fixing hook 63 which is urged by the spring 64. Since the upper surface portion of the claw 63a with which the monitor 33a makes contact is formed slantingly, the claw 63a retracts against the urging force of the spring 64 as the monitor 33a moves downward. When the monitor 33a has moved to a predetermined position, the claw 63a of the fixing hook 63 is brought into engagement with the shoulder portion 62 formed in the rear surface of the monitor 33a by means of the urging force of the spring 64, whereby the monitor 33a is fixed to the casing 60.

When the monitor 33a is to be removed from the casing 60, the moving claw 67 of the fixing hook 63 is moved in a direction indicated by an arrow A against the urging force of the spring 64 to remove the claw 63a from the shoulder portion 62 and thereby remove the monitor 33a from the casing 60. The other structure and operation are the same as those of the above-described embodiment.

In the above-described embodiments, the industrial endoscope apparatus employing the electronic endoscope has been described. However, the present invention can also be applied to an optical endoscope in which an adapter is connected to an eyepiece portion of the optical endoscope to observe the image by a monitor.

It is to be understood that various changes and modifications may be made in the invention without departing from the spirit and scope thereof, and that the invention is not limited by any of the details of description, unless otherwise specified.

What is claimed is:

1. An industrial endoscope apparatus comprising:
   an endoscope which is to be inserted into an inspection portion;
   a control device for controlling said endoscope;
   a light source device for supplying an illumination light to a distal end portion of said endoscope;
   a monitor for displaying an image of an object, wherein the display of the image on said monitor is controlled by said control device;
   a casing in which said control device, said light source device and said monitor are contained within one unit; and
   a fixing means for detachably fixing said monitor to said casing.

2. An industrial endoscope apparatus according to claim 1, wherein said monitor is a CRT monitor.

3. An industrial endoscope apparatus according to claim 1, wherein said monitor is an LCD monitor.

4. An industrial endoscope apparatus according to claim 1, wherein said fixing means fixes said monitor accommodated in an accommodating portion provided in said casing by means of a screw means.

5. An industrial endoscope apparatus according to claim 1, wherein said fixing means fixes said monitor disposed in a notch/shoulder portion formed in said casing by means of a screw means with a fixing member therebetween.

6. An industrial endoscope apparatus according to claim 1, wherein said fixing means performs fixing using a screw means by insertion of a connection pin into a through-hole of a fixing member provided on an upper surface of said casing and into a convex portion provided on said monitor.

7. An industrial endoscope apparatus according to claim 6, wherein said monitor is pivotal about said connection pin and is fixed by means of said connection pin at a desired pivot angle.

8. An industrial endoscope apparatus according to claim 1, wherein said fixing means fixes said monitor accommodated in an accommodating portion of said casing by means of a fixing hook having an urging means.

9. An industrial endoscope according to claim 8, wherein said urging means is a spring.

* * * * *